United States Patent
Aono

(10) Patent No.: US 8,584,507 B2
(45) Date of Patent: Nov. 19, 2013

(54) GAS SAMPLE INTRODUCTION DEVICE AND A GAS CHROMATOGRAPH USING THE SAME

(75) Inventor: Akira Aono, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 654 days.

(21) Appl. No.: 12/585,995

(22) Filed: Sep. 30, 2009

(65) Prior Publication Data
US 2010/0107730 A1    May 6, 2010

(30) Foreign Application Priority Data

Nov. 4, 2008 (JP) .................................. 2008-283573

(51) Int. Cl.
*G01N 1/00* (2006.01)
(52) U.S. Cl.
USPC ....................................................... 73/23.41
(58) Field of Classification Search
None
See application file for complete search history.

(56) References Cited

U.S. PATENT DOCUMENTS 3,405,550 A * 10/1968 Bloch .......................... 73/23.35
6,029,499 A *  2/2000 Sittler et al. ................. 73/23.42

* cited by examiner

*Primary Examiner* — Robert R Raevis
(74) *Attorney, Agent, or Firm* — Manabu Kanesaka

(57) ABSTRACT

A gas sample introduction device for introducing sample gas to a gas analyzer includes a measuring tube, a sample gas supply flow path for introducing the sample gas to the measuring tube, a carrier gas supply flow path for introducing carrier gas to the measuring tube, an exhaust flow path for discharging the gas passing through the measuring tube to outside, and a collecting tube for absorbing a component in the sample gas. A first flow path switching device switches between a first state in which the measuring tube is inserted between the sample gas supply flow path and the exhaust flow path, and a second state in which the measuring tube is inserted between the carrier gas supply flow path and the gas analyzer. A second flow path switching device switches between a collecting-tube inserted state and a collecting-tube short-circuited state in which the collecting tube is not inserted.

4 Claims, 4 Drawing Sheets

GAS SAMPLE INTRODUCTION DEVICE AND A GAS CHROMATOGRAPH USING THE SAME

BACKGROUND OF THE INVENTION AND RELATED ART STATEMENT

The present invention relates to a gas sample introduction device for introducing sample gas to a gas analyzer such as a gas chromatograph and a gas chromatograph using the same.

In a gas chromatography analysis for a sample gas, a gas sample introduction device for introducing the sample gas which is a subject of the analysis into a flow of carrier gas supplied to a column, is widely used. For a sample introduction by the gas sample introduction device, there is a system for measuring a predetermined amount of sample gas by a measuring tube provided in a flow path and introducing it to the column; and a system for concentrating the sample gas by a concentration device provided in the flow path and introducing it to the column. Also, a device which can carry out both of the above-mentioned systems by switching is widely used.

FIG. 4 shows the structure of a flow path in a conventional gas sample introduction device with a function of carrying out the gas sample introduction by switching the sample introduction (hereinafter, called a measurement mode) using the above-mentioned measuring tube and the sample introduction (hereinafter, called a concentration mode) using the concentration device. An eight-direction valve 110 can be manually or mechanically switched to two states between a connected state shown in full lines and a connected state shown in dotted lines in FIG. 4. SVa to SVe are electromagnetic valves, and Ta to Tc are branched tubes. Incidentally, NO of each electromagnetic valve represents a normal open port, NC of each electromagnetic valve represents a normal closed port, and C of each electromagnetic valve represents a common port. Incidentally, although a gas inlet 162 and a mass flow controller 150 are used for supplying a predetermined flow rate of pressured gas in a sample container 200 or dry purge gas in a concentration device 130, the details are omitted in this specification.

First, operations at the time of the measurement mode in the device in FIG. 4 will be explained. When the eight-direction valve 110 is set in the connected state shown in the dotted lines and the electromagnetic valves SVd, SVe are set in NO sides (i.e., C sides and NO sides are connected), the sample gas collected from the sample container 200 by a needle 140 passes through a measuring tube 120 via ports d, e, and then, is discharged from a gas outlet 172 via ports h, a, the electromagnetic valve SVd, and the branched tube Ta. Incidentally, carrier gas supplied to a gas inlet 161 from a gas cylinder and the like (not shown) is sent to a column for analysis via the electromagnetic valve SVe, the ports f, g, the branched tube Tc, and a gas outlet 171.

In the state wherein the sample gas is flowed into the measuring tube 120 as mentioned above, the eight-direction valve 110 is switched to the connected state shown in the full lines in FIG. 4. Hereby, the carrier gas passes through the measuring tube 120 via the ports f, e, and a certain amount of sample gas which is determined by the inner volume of the measuring tube 120 retained in the measuring tube 120 is pushed to the carrier gas, and sent to the column for analysis via the ports h, g, and the branched tube Tc. Incidentally, the sample gas sent to the column is separated by each component in a process of passing through the column, and sequentially detected by a detector via the column.

Subsequently, operations at the time of the concentration mode will be explained. When the eight-direction valve 110 is set in the connected state shown in the full lines, the electromagnetic valve SVe is set to an NO side, and also the electromagnetic valve SVc is set to an NC side, the sample gas collected by the needle 140 passes through a collecting tube 131 provided in the concentration device 130 via the ports d, c, and then, is discharged from the gas outlet 172 through the electromagnetic valve SVc and the branched tube Ta. At this time, the collecting tube 131 is cooled down by cooling means (not shown), and in the process wherein the sample gas passes through the collecting tube 131, a predetermined component (sample component) in the sample gas can be absorbed into the collecting tube 131. Incidentally, at this time, the carrier gas supplied from the gas inlet 161 flows into the column via the electromagnetic valve SVe, ports f, e, measuring tube 120, ports h, g, branched tube Tc, and gas outlet 171.

As mentioned above, after the sample component is absorbed into the collecting tube 131, the eight-direction valve 110 is switched to the connected state shown in the dotted lines, the electromagnetic valve SVc is switched to the NO side, and the electromagnetic valve SVe is switched to the NC side. Then, the carrier gas passes through the collecting tube 131 via the electromagnetic valve SVe, branched tube Tb, and the electromagnetic valve SVc in a direction opposite to the previous sample gas. In this state, when the collecting tube 131 is rapidly heated by heating means (not shown), the sample component which has been absorbed into the collecting tube 131 is desorbed at once, so that the sample component in high concentration outflows from the collecting tube 131 with a carrier gas flow, and is introduced to the column via the ports c, b and branched tube Tc. According to the above-mentioned concentration mode, even if the sample component contained in the original sample gas has a small amount, this can be sent to the column after concentration, so that detection sensitivity can be improved.

As mentioned above, in the gas sample introduction device having the conventional function of switching the measurement mode and the concentration mode, the measuring tube 120 and the collecting tube 131 are connected in parallel, and the sample gas which has been sent from one of the measurement mode and the concentration mode flows into the column through the branched tube Tc provided immediately before the column. However, since the gas does not flow in a pipe on a collecting tube 131 side of the branched tube Tc at the time when the measurement mode is carried out, there was a possibility that a part of the sample gas sent from the measuring tube 120 might move into the pipe on the collecting tube 131 side by spreading. Similarly, since the gas does not flow in the pipe on the measuring tube 120 side of the branched tube Tc at the time when the concentration mode is carried out, there was a possibility that a part of the sample gas sent from the collecting tube 131 might move into the pipe on the measuring tube 120 side by spreading. If the sample gas spreads as above, a collection rate (rate between the sample gas introduced to the column and the sample gas collected from the sample container 200) of the sample gas is reduced, so that negative effects can be exerted on analytical sensitivity or analytical precision. Also, the sample gas moved into an unintended pipe may be introduced to the column through the branching tube Tc at the time of the next analysis, and this may have an effect on a result of the analysis.

The present invention has been made in order to solve the above-mentioned problem, and an object of this invention is to provide a gas sample introduction device which can carry out the gas sample introduction by switching between the measurement mode and the concentration mode, prevent the sample gas from spreading to the unintended pipe, and improve the analytical sensitivity or analytical precision in a gas analysis and reliability of the analysis, and the gas chromatograph using the same.

Further objects and advantages of the invention will be apparent from the following description of the invention.

SUMMARY OF THE INVENTION

The invention which has been made in order to solve the above-mentioned problem is a gas sample introduction device for introducing sample gas to a gas analyzer. The gas sample introduction device comprises:

a measuring tube having a predetermined volume;

a sample gas supply flow path for introducing the sample gas to the measuring tube;

a carrier gas supply flow path for introducing the carrier gas to the measuring tube;

an exhaust flow path for discharging the gas which has passed the measuring tube to the outside;

concentration means including a collecting tube for absorbing a predetermined component in the sample gas and concentrating the sample gas by a thermal desorption method;

first flow path switching means for switching a first state wherein the measuring tube is inserted between the sample gas supply flow path and the exhaust flow path and a second state wherein the measuring tube is inserted between the carrier gas supply flow path and the gas analyzer; and second flow path switching means for switching, in the first state and the second state, a collecting-tube inserted state wherein the collecting tube is inserted between the measuring tube and the exhaust flow path or between the measuring tube and the gas analyzer, and a collecting-tube short-circuited state wherein the collecting tube is not inserted.

In the gas sample introduction device according to the invention having the above-mentioned structure, when a measurement mode is carried out, after the second flow path switching means is set in the collecting-tube short-circuited state, the first flow path switching means is set in the first state. Herewith, a flow path from the sample gas supply flow path to the exhaust flow path is formed through the measuring tube, and the sample gas passes through the measuring tube. After that, if the first flow path switching means is in the second state, a flow path from the carrier gas supply flow path to the gas analyzer is formed through the measuring tube. As a result, a predetermined amount of sample gas retained in the measuring tube is introduced to the gas analyzer with a flow of the carrier gas.

On the other hand, when the concentration mode is carried out, after the second flow path switching means is set in the collecting-tube inserted state, the first flow path switching means is set in the first state. Herewith, a flow path from the sample gas supply flow path to the exhaust flow path is formed through the measuring tube and the collecting tube. This time, by cooling the collecting tube by predetermined cooling means, a predetermined component in the sample gas passing through the collecting tube is absorbed in the collecting tube. Incidentally, without providing the cooling means, the predetermined component may be absorbed at room temperature. After that, if the first flow path switching means is set in the second state, the flow path from the carrier gas supply means to the gas analyzer is formed through the measuring tube and the collecting tube. By heating the collecting tube by predetermined heating means, the sample component absorbed in the collecting tube is desorbed, and introduced to the gas analyzer with the flow of the carrier gas.

More specifically, the gas sample introduction device of the present invention can connect the measuring tube and the collecting tube in series when the concentration mode is carried out, and the collecting tube can be short-circuited in the flow path of the sample gas when the measurement mode is carried out. Thus, when each mode is carried out, the gas sample introduction device can prevent the sample component from spreading to a pipe on an unused side.

Incidentally, a switching operation of the flow path by the first flow path switching means and/or the second flow path switching means may be carried out manually by a user, or carried out according to a predetermined program or a instruction of the user using driving means such as a motor and the like.

Additionally, the gas sample introduction device of the present invention includes:

a dry purge gas supply flow path for introducing dry purge gas to the collecting tube; and a dry purge gas exhaust flow path for discharging the dry purge gas passed through the collecting tube to the outside. In the second flow path switching means, it is preferred that the collecting tube be inserted between the dry purge gas supply flow path and the dry purge gas exhaust flow path in the collecting-tube short-circuited state.

Also, the gas chromatograph of the present invention comprises a column; the gas sample introduction device introducing the sample gas to the column; and a detector for detecting the sample component separated by the column, wherein the gas sample introduction device of the present invention is employed as the gas sample introduction device.

As explained above, according to the invention, the gas sample introduction device which can be carried out by switching between the measurement mode and the concentration mode can prevent the sample gas from spreading to unintended pipe. Thus, a residue of a sample or a deterioration of a collection rate due to the spreading of the sample gas can be prevented, and sensitivity and precision of gas analysis can be improved. Also, an analysis with high reliability is possible.

DETAILED DESCRIPTION OF PREFERRED EMBODIMENTS

Figure 1:
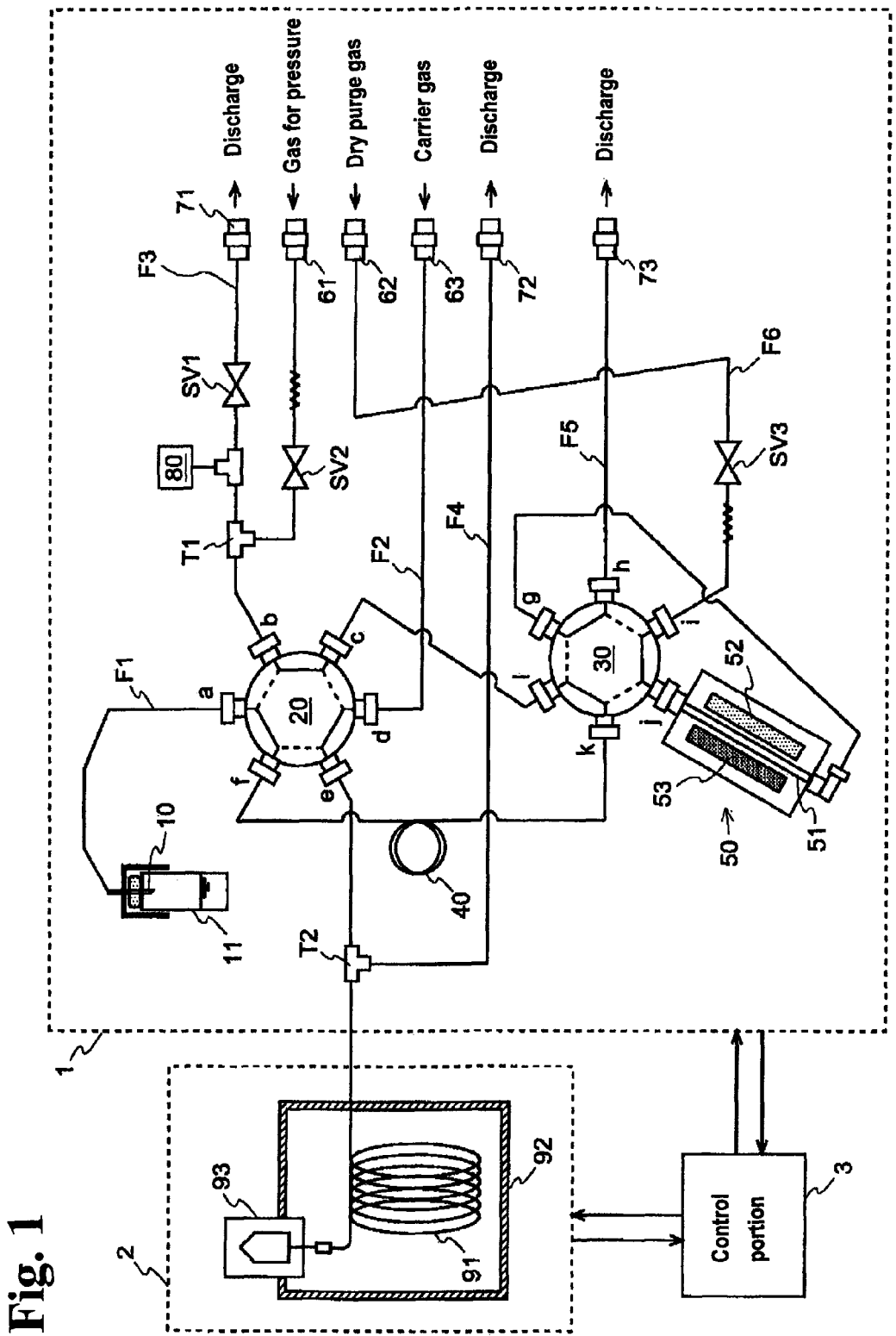
FIG. 1 is a schematic structural view of a gas chromatograph using a gas sample introduction device according to an embodiment of the present invention.

Hereunder, embodiments of a gas sample introduction device of the present invention will be explained with reference to the attached drawings. FIG. 1 is a structural view mainly showing a flow path of a gas chromatograph using the gas sample introduction device of the embodiment.

As shown in FIG. 1, the gas chromatograph according to the embodiment broadly comprises a sample introduction portion 1, an analysis portion 2, and a control portion 3. The sample introduction portion 1 includes two flow path switching valves 20, 30, a measuring tube 40, and a sample concentration unit 50, and the analysis portion 2 includes a column oven 92, an analysis column 91, and a detector 93.

In the sample introduction portion 1, the first flow path switching valve 20 and the second flow path switching valve 30 are rotary valves with 6 ports and 2 positions including 6 ports of the respective ports a to f or ports g to l. Under the control of the control portion 3, the valves 20, 30 are alternatively switched to a connected state shown in full lines or a connected state shown in dotted lines in FIG. 1.

In the port a of the first flow path switching valve 20, a needle 10 for collecting sample gas is connected, and the end of the needle 10 is disposed so as to position in an upper space (headspace) of a sample container 11. In the port b, a gas inlet 61 for introducing gas (pressured gas) for pressurizing the inside of the sample container 11 is connected to a gas outlet 71 for discharging the sample gas through a branched tube T1. On a flow path between the branched tube T1 and the gas inlet 61, an electromagnetic valve SV2 is provided, and on the flow path between the branched tube T1 and the gas outlet 71, an electromagnetic valve SV1 and a pressure sensor 80 are provided. The port d is connected to a gas inlet 63 for introducing carrier gas, and the port e is connected to the end of the inlet of the column 91 and a split flow path F4 through a branched tube T2. The split flow path F4 is used for discharging a part of the sample gas without sending to the column 91, and in the end of the split flow path F4, a gas outlet 72 for discharging the sample gas is provided. Also, the port c is connected to the port l of the second flow path switching valve 30, and the port f is connected to the port k of the second flow path switching valve 30 through the measuring tube 40 containing a predetermined volume. On the other hand, the port i of the second flow path switching valve 30 is connected to a gas inlet 62 for introducing dry purge gas hereinafter described through an electromagnetic valve SV3, and the port h is connected to a gas outlet 73 for discharging the dry purge gas, respectively. A collecting tube 51 of the sample concentration unit 50 is connected between the ports g, j. Incidentally, although a split method is used for the sample introduction portion 1 here, it is natural that a splitless method may be used.

For the collecting tube 51, a tube wherein a predetermined adsorbent is applied to the inner face of a hollow tube or a tube wherein the predetermined adsorbent is filled in the hollow tube, can be used. In addition to the above-mentioned collecting tube 51, the sample concentration unit 50 includes a cooling portion 52 for cooling the collecting tube 51 and a heating portion 53 for heating the collecting tube 51. For example, the heating portion 53 can be structured by a heater and the like provided so as to contact with the collecting tube 51, and the cooling portion 52 can be structured so as to cool the collecting tube 51 by circulating a predetermined refrigerant into a refrigerant pipe provided so as to contact with the collecting tube 51, or so as to cool by a Peltiert element.

In the sample introduction portion 1, the first flow path switching valve 20 corresponds to the first flow path switching means of the present invention, and the respective connected states shown in full lines and dotted lines in the valve 20 correspond to the first and second states of the present invention. Also, the second flow path switching valve 30 corresponds to second flow path switching means of the present invention, and the respective connected states shown in dotted lines and full lines in the valve 30 correspond to a collecting-tube inserted state and a collecting-tube short-circuited state of the invention. In addition, a flow path F1 connected to the port a of the first flow path switching valve 20 and a flow path F2 connected to the port d correspond to a sample gas supply flow path and a carrier gas supply flow path of the invention, respectively. A flow path F3 between the port b and the gas outlet 71 corresponds to an exhaust flow path of the invention. Moreover, a flow path F5 connected to the port h of the second flow path switching valve 30 corresponds to a dry purge gas exhaust flow path of the invention, and a flow path F6 connected to the port i corresponds to a dry purge gas supply flow path of the invention.

Incidentally, the gas inlets 61, 62 and the gas outlet 71 are connected to a pressure control portion (not shown), and gas pressure flowing through the gas inlets 61, 62 and the gas outlet 71 is controlled by the pressure control portion. On the other hand, the gas inlet 63 and the gas outlets 72, 73 are controlled by a mass flow control portion (not shown), and the mass flow of the gas flowing through the gas inlet 63 and the gas outlets 72, 73 is controlled by the mass flow control portion. Incidentally, the pressure control portion and the mass flow control portion may be electronically controlled or manually controlled.

The control portion 3 controls opening and closing operations of the electromagnetic valves SV1 to SV3 of the sample introduction portion 1, switching operations of each flow path switching valves 20, 30, and operations of the pressure control portion, mass flow control portion, and the like. Also, the control portion 3 controls operations of the column oven 92 and the detector 93 of the analysis portion 2. For example, the control portion 3 is realized by a personal computer and according to a predetermined control program; the above-mentioned respective operations are controlled, so that the measurement or concentration of the sample gas and the introduction of the sample gas to the column can be carried out.

The sample introduction portion 1 of the embodiment introduces the sample gas by a headspace method. In the sample introduction portion 1, a liquid sample (or a solid sample) housed in the sample container 11 is heated, and a volatilized sample component is collected from the upper space in the container and introduced to the column 91. Hereinafter, operations of the sample introduction portion 1 at the time of the sample gas introduction will be explained.

1. Measurement Mode

First, operations in the case of a sample infusion (hereinafter, called the measurement mode) by using the measuring tube will be explained. Incidentally, at the time of the measurement mode, constantly, the second flow path switching valve 30 is set in the connected state shown in the full lines, so that the following series of operations are carried out in a state wherein the collecting tube 51 is short-circuited in the flow paths of the sample gas and the carrier gas.

(i) Pressurization Process

First, after the first flow path switching valve 20 is set in the connected state shown in the full lines, the sample container 11 is heated to a predetermined temperature by heating means (not shown) and set in a vapor-liquid equilibrium state. After that, the electromagnetic valve SV2 is opened, and pressurized gas is introduced from the gas inlet 61, so that the inside of the sample container 11 is set to have a predetermined pressure.

(ii) Sample Gas Introduction Process to Measuring Tube

Next, when the electromagnetic valve SV2 is closed and the electromagnetic valve SV1 is opened, the gas (sample gas) containing the vaporized sample component inside the sample container 11 flows into the measuring tube 40 via the needle 10. At this time, the sample gas passed through the measuring tube 40 is discharged from the gas outlet 71. Incidentally, during the above-mentioned process, the carrier gas flows from the gas inlet 63 to the column 91 or the gas outlet 72 through the first flow path switching valve 20.

(iii) Sample Gas Sending Process to Column

After that, if the first flow path switching valve 20 is set in the connected state shown in the dotted lines, the carrier gas supplied from the gas inlet 63 flows to the column 91 via the measuring tube 40. Hereby, a predetermined amount of sample gas retained in the measuring tube 40 is introduced to the column 91 with the flow of the carrier gas. Incidentally, parts of the carrier gas and the sample gas that flowed out of the port e of the first flow path switching valve 20 flow into the split flow path F4 at a predetermined split ratio, and are discharged from the gas outlet 72. The sample component in the sample gas introduced to the column 91 is temporally-separated in the process of passing through the column 91, and sequentially detected by the detector 93 connected to the end of the outlet of the column 91.

2. Concentration Mode

Next, operations in the case wherein the sample introduction (hereinafter, called the concentration mode) using the sample concentration unit 50 will be explained.

(i) Pressurization Process

First, after the first flow path switching valve 20 and the second flow path switching valve 30 are set in the connected state shown in the full lines, the sample container 11 is heated and pressured in a fashion same as the measurement mode.

(ii) Sample Component Adsorption Process

After that, when the electromagnetic valve SV2 is closed, the second flow path switching valve 30 is set in the connected state shown in the dotted lines, and also the electromagnetic valve SV1 is opened, the sample gas inside the sample container 11 flows into the collecting tube 51 via the needle 10 and the measuring tube 40. At this time, since the collecting tube 51 is cooled to a predetermined temperature by the cooling portion 52, a predetermined component in the sample gas is adsorbed to the inside of the collecting tube 51 in the process wherein the sample gas passes through the collecting tube 51. Incidentally, the sample gas after the sample component has been adsorbed is discharged from the gas outlet 71.

(iii) Dry Purge Process

In the sample component adsorption process, moisture in the sample gas is also adsorbed in the collecting tube 51 with the sample component which is an analysis subject. Therefore, a water removal treatment (dry purge) is required beforehand so that the moisture is not sent to the column 91 at the time of the analysis. In this dry purge process, the second flow path switching valve 30 is switched to the connected state shown in the full lines, and also the electromagnetic valve SV3 is opened, so that a flow path to the gas outlet 73 which passes through the collecting tube 51 from the gas inlet 62 is formed. Hereby, dry purge gas such as drying He gas and the like passes through the flow path, and the moisture inside the collecting tube 51 is discharged from the gas outlet 73 with the dry purge gas.

(iv) Desorption and Sending Process of Sample Component to Column

When the dry purge process is completed, the first flow path switching valve 20 and the second flow path switching valve 30 are switched to the connected state shown in the dotted lines, and the collecting tube 51 is heated by a predetermined timing by the heating portion 53, so that the sample component is desorbed from the collecting tube 51. Hereby, the carrier gas supplied from the gas inlet 63 passes through the collecting tube 51 and the measuring tube 40 and is followed into the column 91. Accordingly, the sample component desorbed from the collecting tube 51 is introduced to the column 91 with the carrier gas. Incidentally, a part of the carrier gas containing the sample component flows into the split flow path F4 at the predetermined split ratio, and is discharged from the gas outlet 72.

Figure 2:
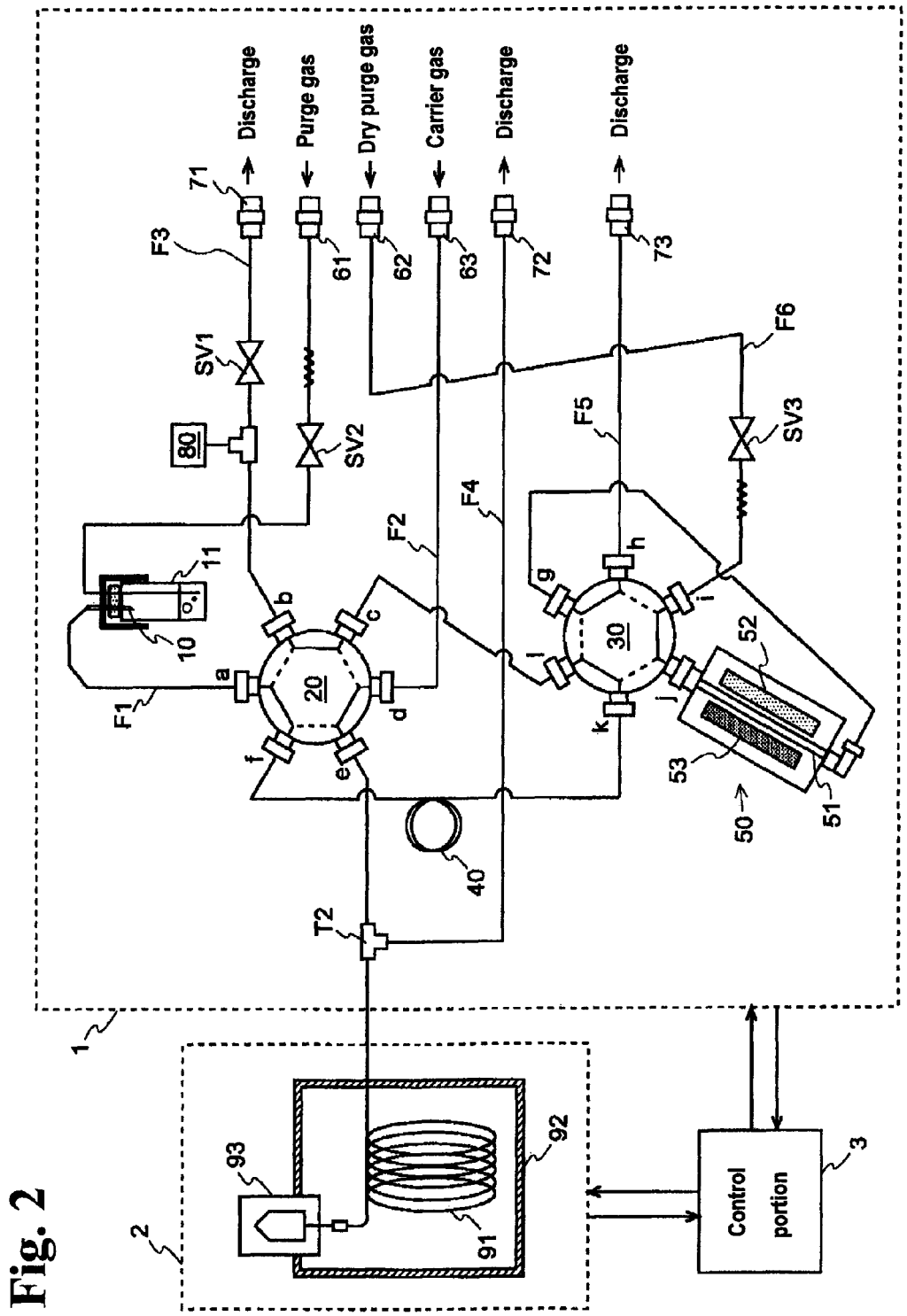
FIG. 2 is a schematic structural view of the gas chromatograph using the gas sample introduction device according to another embodiment of the present invention.
Figure 3:
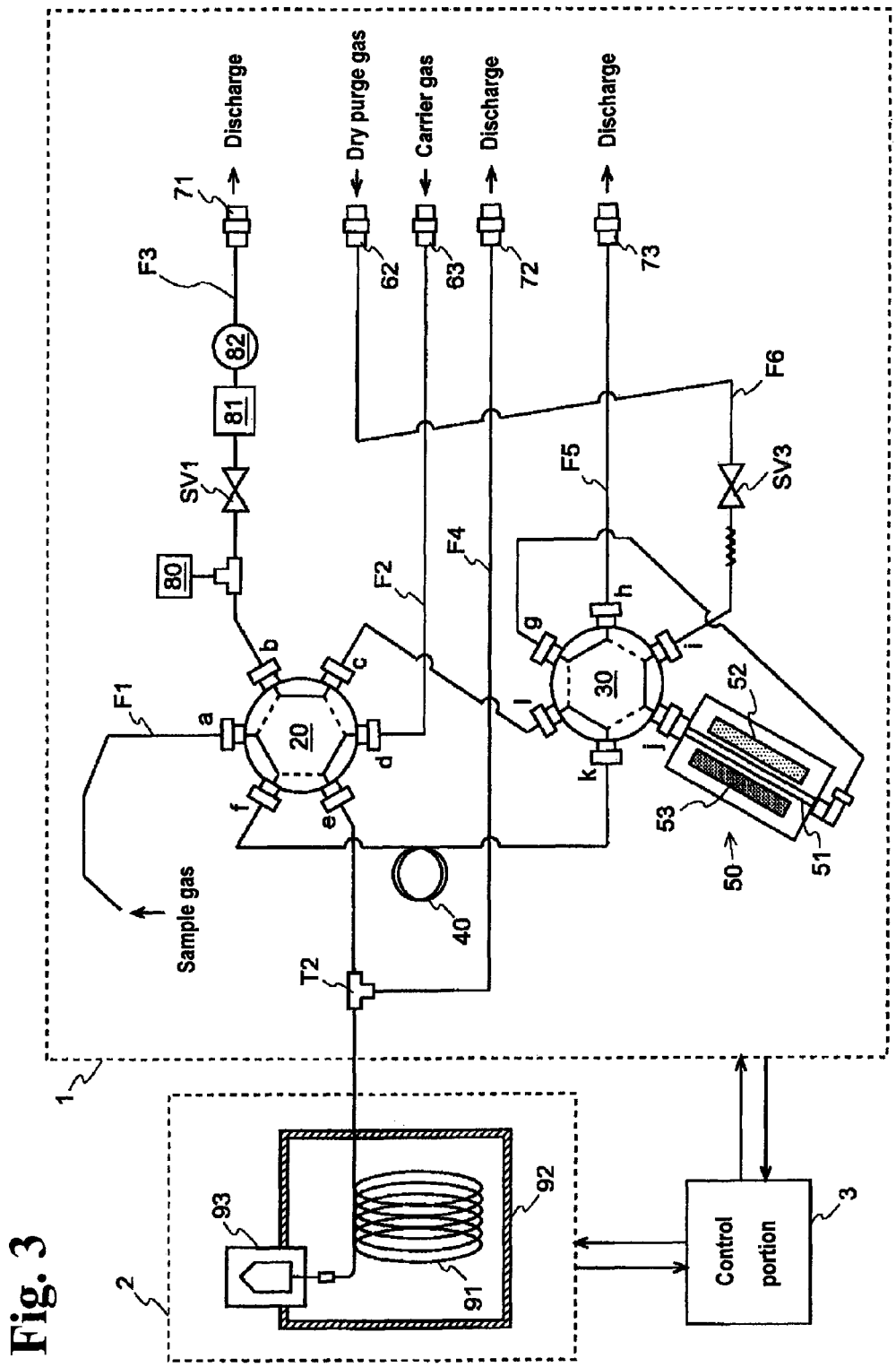
FIG. 3 is a schematic structural view of the gas chromatograph using the gas sample introduction device according to another embodiment of the present invention.
Figure 4:
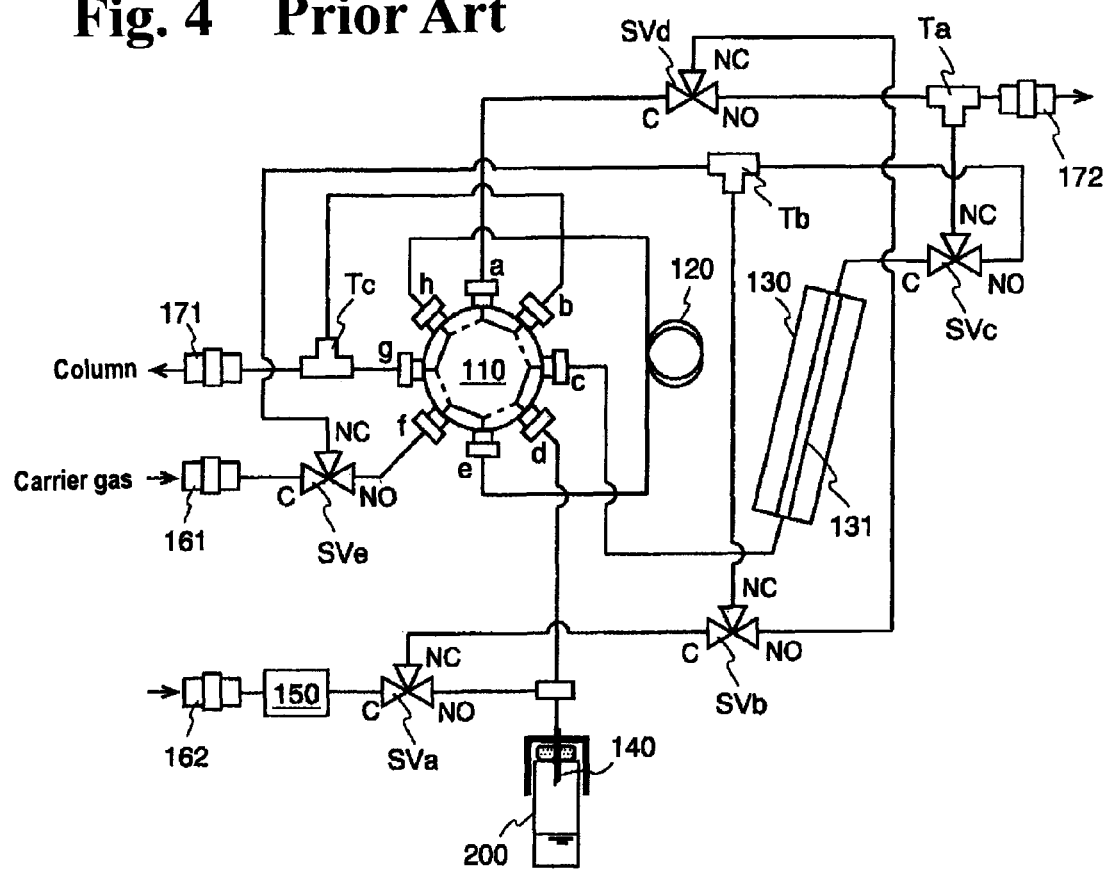
FIG. 4 is a schematic view showing an example of the structure of a flow path of a conventional type gas sample introduction device.

As stated above, preferred embodiments for carrying out the present invention using the embodiments have been explained. However, the invention is not limited to the above-mentioned embodiments, and can be modified accordingly within a scope of the purpose of the invention. For example, in the embodiment, the introduction of the sample gas by the headspace method is carried out. However, the introduction method of the sample is not limited to this, and various methods can be used. FIGS. 2, 3 show examples of the gas chromatograph including the gas sample introduction device by other sample introduction methods.

FIG. 2 shows a method of collecting the sample gas by forcibly removing volatile organic compound or musty smell and the like from water by infusing sample liquid with purge gas. This example has the same flow path structure as the above-mentioned embodiment except that the other end of the flow path which is connected to the gas inlet 61 is inserted into the sample container 11 instead of being connected to the branched tube T1. In the sample introduction device having the above-mentioned structure, both the measurement mode and concentration mode carry out bubbling (aeration processing) of the sample liquid instead of the pressurization process. In the bubbling process, by setting the first flow path switching valve 20 in the connected state shown in the dotted lines in FIG. 2, and opening the electromagnetic valve SV2, the purge gas such as the He gas and the like is introduced from the gas inlet 61, and the sample liquid is carried out with the bubbling (aeration processing). Hereby, the volatile organic compound and the like in the liquid are driven to the upper space in the sample container 11. Accordingly, after that, in a fashion same as the embodiment, the gas inside the upper space is collected by the needle 10, measured or concentrated, and introduced to the column 91.

Also, FIG. 3 shows a method of collecting the sample gas by sucking it by a pump. The device in FIG. 3 has a flow path structure same as that of the embodiment, except that there is no flow path (flow path between the gas inlet 61 and the branched tube T1 in FIG. 1) for pressuring the sample container, and that there is a pump 82 for sucking the sample gas between the electromagnetic valve SV1 and the gas outlet 71 and a mass flow controller 81 for controlling a flow rate at the time of sucking the sample gas. In the sample introduction device having the above-mentioned structure, both the measurement mode and the concentration mode do not carry out the above-mentioned pressurization process. In the "sample introduction process to the measuring tube" of the measurement mode, or the "sample component adsorption process" of the concentration mode, after the first flow path switching valve 20 is set in the connected state shown in the full lines in FIG. 3, the electromagnetic valve SV1 is opened and the pump 82 is driven. Hereby, the sample gas housed in a predetermined sample gas container and the like is sucked via the flow path F1 connected to the port a of the first flow path switching valve 20, and discharged from the gas outlet 71 through the measuring tube 40 (or the measuring tube 40 and the collecting tube 51). Other operations are the same as those of the embodiment.

The disclosure of Japanese Patent Application No. 2008-283573, filed on Nov. 4, 2008, is incorporated in the application.

While the invention has been explained with reference to the specific embodiments of the invention, the explanation is illustrative and the invention is limited only by the appended claims.

What is claimed is:

1. A gas sample introduction device for introducing sample gas to a gas analyzer, comprising:
   a measuring tube having a predetermined volume;
   a sample gas supply flow path for introducing the sample gas to the measuring tube;
   a carrier gas supply flow path for introducing carrier gas to the measuring tube;
   an exhaust flow path for discharging the gas which has passed through the measuring tube to outside;
   concentration means including a collecting tube for absorbing a predetermined component in the sample gas and concentrating the sample gas;
   first flow path switching means for switching between a first measuring state in which the measuring tube is inserted between the sample gas supply flow path and the exhaust flow path, and a second measuring state in which the measuring tube is inserted between the carrier gas supply flow path and the gas analyzer; and
   second flow path switching means for switching, in the first and the second measuring states, between a first collecting-tube state in which the collecting tube is inserted between the measuring tube and the exhaust flow path or between the measuring tube and the gas analyzer, and a second collecting-tube state in which the collecting tube is not inserted,
   wherein the component which has been absorbed into the collecting tube is desorbed at once, so that the component in high concentration outflow from the collecting tube is transmitted to a detector.

2. A gas sample introduction device according to claim 1, further comprising:
   a dry purge gas supply flow path for introducing dry purge gas to the collecting tube; and
   a dry purge gas exhaust flow path for discharging the dry purge gas which has passed through the collecting tube to the outside, wherein the second switching means is arranged such that the collecting tube is located between the dry purge gas supply flow path and the dry purge gas exhaust flow path in the second collecting-tube state.

3. A gas chromatograph, comprising:
   the gas sample introduction device according to claim 1 for introducing the sample gas to the gas analyzer, wherein the gas analyzer comprises:
   a column for separating a sample component from the sample gas; and
   a detector for detecting the sample component separated by the column.

4. A gas sample introduction device for introducing sample gas to a gas analyzer, comprising:
   a measuring tube having a predetermined volume;
   a sample gas supply flow path for introducing the sample gas to the measuring tube;
   a carrier gas supply flow path for introducing carrier gas to the measuring tube;
   an exhaust flow path for discharging the gas which has passed through the measuring tube to outside;
   concentration means including a collecting tube for absorbing a predetermined component in the sample gas and concentrating the sample gas;
   first flow path switching means for switching between a first measuring state in which the measuring tube is inserted between the sample gas supply flow path and the exhaust flow path, and a second measuring state in which the measuring tube is inserted between the carrier gas supply flow path and the gas analyzer; and
   second flow path switching means for switching, in the first and the second measuring states, between a first collecting-tube state in which the collecting tube is inserted between the measuring tube and the exhaust flow path or between the measuring tube and the gas analyzer, and a second collecting-tube state in which the collecting tube is not inserted,
   wherein said concentration means includes a heating portion for heating the collecting tube and a cooling portion for cooling the collecting tube for thermal desorption method.

* * * * *